US 6,697,101 B1

(12) United States Patent
Takahashi et al.

(10) Patent No.: US 6,697,101 B1
(45) Date of Patent: Feb. 24, 2004

(54) ELECTRONIC ENDOSCOPE

(75) Inventors: Akihiro Takahashi, Tokyo (JP); Kohei Iketani, Saitama (JP)

(73) Assignee: Pentax Corporation, Tokyo (JP)

( * ) Notice: Subject to any disclaimer, the term of this patent is extended or adjusted under 35 U.S.C. 154(b) by 446 days.

(21) Appl. No.: 09/664,829

(22) Filed: Sep. 19, 2000

(30) Foreign Application Priority Data

Sep. 20, 1999 (JP) .......................................... P11-265041

(51) Int. Cl.[7] .................................................. H04N 7/18
(52) U.S. Cl. .......................................... 348/71; 348/65
(58) Field of Search ............... 348/65–76; 600/107–120

(56) References Cited

U.S. PATENT DOCUMENTS

| 4,799,104 A | * | 1/1989 | Hosoya et al. ................. 348/71 |
| 5,305,098 A | * | 4/1994 | Matsunaka et al. ............ 348/65 |
| 5,877,802 A | * | 3/1999 | Takahashi et al. ............. 348/71 |
| 5,902,230 A | | 5/1999 | Takahashi et al. |
| 6,491,628 B1 | * | 12/2002 | Kobayashi .................. 600/168 |
| 6,545,703 B1 | * | 4/2003 | Takahashi et al. ............. 348/69 |

\* cited by examiner

*Primary Examiner*—Andy Rao
(74) *Attorney, Agent, or Firm*—Greenblum & Bernstein, P.L.C.

(57) ABSTRACT

An electronic endoscope has a video-scope having an image sensor and a video-processor. The video-scope is connected to the video-processor, to which a computer system, having a display unit and a digital recorder, is connected. The image-pixel signals corresponding to an object image, formed on the image sensor, are read from the image sensor and processed to obtain digital video signals. The digital video signals are generated in accordance with a square-pixel frequency, which is a sampling frequency for the computer system. The digital video signals are fed to the computer system to display the object image on the display unit, and/or record the object image in the digital recorder.

15 Claims, 5 Drawing Sheets

ELECTRONIC ENDOSCOPE

BACKGROUND OF THE INVENTION

1. Field of the Invention

The present invention relates to an electronic endoscope having a video-scope and a video-processor, and especially relates to the transmission of digital video signals.

2. Description of the Related Art

In a conventional electronic endoscope, an image sensor, such as a CCD, is provided at a distal end of a video-scope, and an object image is formed on the image sensor when the video-scope is inserted into a body-cavity. In a video-processor, image-pixel signals, read from the image sensor, are subjected to various processes so that video signals corresponding to the object image are generated. The video signals are fed to a TV monitor, thus the object image, such as the inner wall of a stomach, is displayed on the monitor. Recently, not only analog video signals but also digital video signals can be transmitted from the video-processor to the monitor and other peripheral apparatus including a video recorder. As there is less degradation of the digital video signals during transmission compared to the analog video signals, an object image of better quality can be displayed on the monitor.

Normally, the digital video signals are generated and processed in accordance with a color TV standard, such as NTSC. A display unit and a video recorder corresponding to the color TV standard are used with the electronic endoscope. On the other hand, in the medical field, computer systems have recently been utilized for filing of the observed image, patient's list and so on. However, processing of the digital video signal for the computer system is different from the TV standard. Therefore, when using a display and a filing system for a computer, the degradation of the video signals occurs in the process of transmission, and the picture quality decreases.

SUMMARY OF THE INVENTION

Therefore, an object of the present invention is to provide an electronic endoscope system capable of transmitting digital video signals to the computer system, while limiting the degradation of picture quality.

An electronic endoscope according to the present invention has a video-processor and a video-scope. The video-scope has an image sensor, and is detachably connected to the video-processor. A computer is also connected to the video-processor. An object image is formed on the image sensor, thus image-pixel signals corresponding to the object image a regenerated. The image-pixel signals are read from the image sensor, and the video-processor processes the image-pixel signals to obtain video signals. The video-processor has a video signal processor and a first pulse generator. The video signal processor generates digital video signals on the basis of the image-pixel signals and outputs the signals to the computer. The first pulse generator for the video signal processor feeds clock pulses to the video signal processor in accordance with a sampling frequency, such that the digital video signals are generated and output to the computer in accordance with the sampling frequency. The sampling frequency corresponds to a square-pixel frequency for the computer.

For digital processing of video signals, the sampling frequency for a computer is different to the sampling frequency for a digital TV standard. According to the present invention, digital video signals are generated and output to the computer in accordance with a square-pixel frequency corresponding to a computer video standard. Therefore, when transmitting the digital video signals to the computer and processing the signals in the computer, adverse degradation of the video signals does not substantially occur during the digital processing. Consequently, picture quality is maintained. When the TV standard is a NTSC standard, applied in America and Japan and so on, the square-pixel frequency is 12.2727 MHz. Where the PAL standard is applied, in Europe, Australia and so on, the square-pixel frequency is 14.75 MHz.

Preferably, the sampling frequency to the video signal processor is set to "n" times the square-pixel frequency or "1/n" times the square-pixel frequency. Herein, "n" represents integers.

Preferably, a digital recorder for recording the object image as digital image data is connected to the computer, and a display unit, for displaying the object image, is also connected. Note that, the display unit corresponds to a computer video standard, such as the VGA standard and the digital image data is recorded in the digital recorder, such as a CD-R (Compact Disc-Recordable) in accordance with the square pixel frequency. When the digital video signals are fed to the display unit and the digital recorder, the object image with high picture quality is displayed on the display unit, and is recorded by the digital recorder if required.

For color image photographing, as an example, a R, G, B sequential method is applied. Thus, the image-pixel signals are transformed to digital R, G, B signals, which correspond to red color, green and blue color respectively. Preferably, the video signal processor has a matrix circuit and a multiplexer. The matrix circuit transforms the digital R, G, B signals to digital luminance signals and digital color difference signals. The multiplexer processes the digital luminance signals and the digital color difference signals. Consequently, multiplexed digital video signals are generated as the digital video signals. Thus, the multiple digital video signals are transmitted between networked computer apparatus via a LAN (Local Area Network), i.e., an Ethernet.

Preferably, the multiplexer generates the multiple digital video signals such that a ratio of the sampling frequency of the digital luminance signals and the sampling frequency of the digital color difference signals in the multiplexed digital video signals becomes "4:2:2". This ratio depends upon a ratio of the digital TV standard. For example, the clock frequency of clock pulses fed to the matrix circuit is the same as the square-pixel frequency, and the clock frequency of clock pulses fed to the multiplexer is two times the square-pixel frequency.

Preferably, the video signal processor further includes a parallel/serial converter. The parallel/serial converter transforms the multiple digital video signals, which are digital parallel video signals, to digital serial video signals to send to the computer. Note that, the first pulse generator feeds the clock pulses to the parallel/serial converter in accordance with the square-pixel frequency. As the digital serial video signals are transmitted, a low cost cable for serial transmission compared to a cable for parallel transmission can be used. Namely, a hardware cost saving is achieved.

Preferably, A decoder is provided between the video-processor and the computer for feeding the digital R, G, B signals to the computer. The decoder has a serial/parallel converter, demultiplexer, an inverse matrix circuit and a second pulse generator. The serial/parallel converter transforms the digital serial video signals to multiple digital video signals. The demultiplexer processes the multiple digital video signals to restore the digital luminance signals and the digital color difference signals. The inverse matrix circuit transforms the digital luminance signals and the digital color difference signals to digital R, G, B signals. The second pulse generator for the decoder feeds clock pulses to the serial/parallel converter, the demultiplexer and the inverse matrix circuit, in accordance with the square-pixel frequency.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiment of the present invention is described with reference to the attached drawings.

Figure 1:
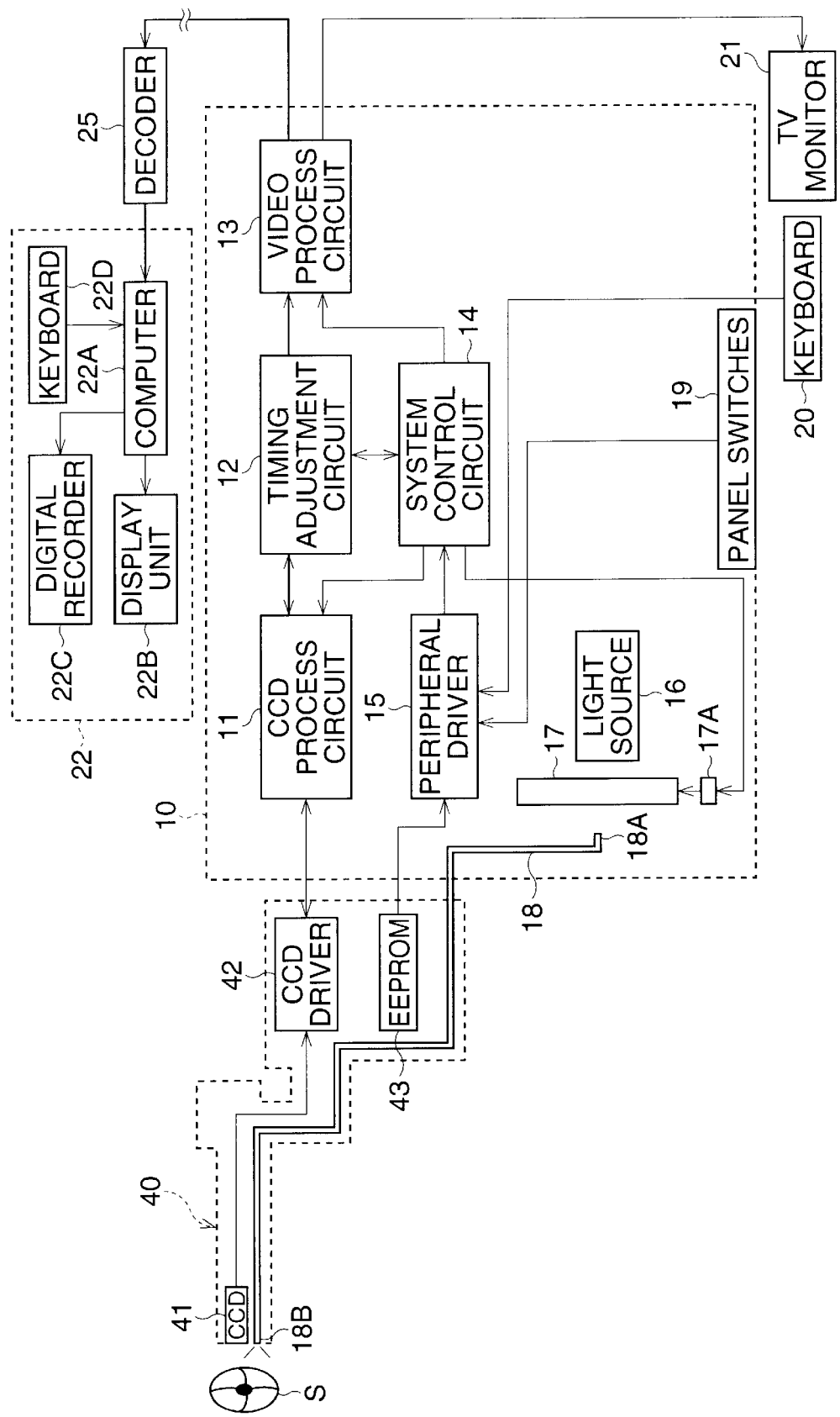
FIG. 1 is a block diagram of an electronic endoscope system of an embodiment.

FIG. 1 is a block diagram of an electronic endoscope system of an embodiment of the present invention.

The electronic endoscope system has an electronic endoscope having a video-scope 40 and a video-processor 10, a TV monitor 21 and a computer system 22. The computer system 22, including a computer 22A, a display unit 22B, keyboard 22D and a digital recorder 22C, is connected to the video-processor 10 via a decoder 25. The video-scope 40 is detachably connected to the video-processor 10, and the TV monitor 21 is connected to the video-processor 10. When an operation using the electronic endoscope is performed, the video-scope 40 is inserted into a body-cavity. In this embodiment, the NTSC standard is used as the color TV standard, and a R (Red), G (Green), B (Blue) sequential process, by which a color filter is incorporated in the video-processor 10, is used as the color image photographing method.

A rotating filter 17 for the R, G, B sequential process has a disk-like shape, on which A red (R), green (G) and blue (B) filter, passing light of corresponding wavelengths respectively, are provided. Each of the R, G, B filters has a fan-like shape, and are arranged at regular intervals. Note that, shield areas are formed between each filter. The rotating filter 17 is driven by a motor 17A and rotates at determined revolutions. Herein, the revolution of the rotating filter 17 is 30 (Hz) to correspond to one frame worth of scanning time (=1/30 sec) with respect to the NTSC standard.

Light, radiated from a light source 16, such as a Halogen lamp, enters in an incident surface 18A of a light guide fiber bundle 18, which is an optical fiber, via the rotating filter 17 and a condenser lens (not shown). The light guide fiber bundle 18, provided through the video-scope 40, passes light from the light source 16 to the distal end of the video-scope 40, and to an object S. The light passing through the light guide fiber bundle 18 exits from an object-side surface 18B of the fiber bundle 18 toward the object S. As the rotating filter 17 turns between the incident surface 18A and the light source 16, light of R (Red), G (Green) and B (Blue) wavelength, corresponding to the red, green and blue filters respectively, is reflected from object S in turn. The reflected light reaches a CCD 31 via an objective lens (not shown). Thus, an object image corresponding to the red, green and blue colors are formed on the CCD 41 in turn.

In the CCD 41 of an image sensor, image-pixel signals corresponding to the object image are generated by photoelectric-conversion. Namely, the image-pixel signals corresponding to the R, G, B colors are generated in turn. When the light from the light source 16 is shielded by one of the shielding areas on the rotating filter 17, one frame worth of image-pixel signals corresponding to one of the R, G, B colors is read from the CCD 41 by a CCD driver 42. In the CCD driver 42, the image-pixel signals are amplified and fed to a CCD process circuit 11 in the video-processor 10.

In the CCD process circuit 11, image-pixel signals are subjected to various processes, such as an analog-digital conversion and a reduction of signal noise, and then fed to the timing adjustment circuit 12. In the timing adjustment circuit 12, the image-pixel signals corresponding to the red, green, blue color, which are sequentially fed from the CCD process circuit 11, are synchronized. Hereinafter, the synchronized image-pixel signals described above are expressed as "digital R, G, B signals".

The timing adjustment circuit 12 has a reading pulse generator (not shown), which generates clock pulses and outputs them to the CCD 41, the CCD driver 42 and the CCD process circuit 11. The process of reading the image-pixel signals from the CCD 41, the analog-to-digital conversion and the synchronization of the image-pixel signals are performed in accordance with the clock pulses from the reading pulse generator. Note that, the frequency of the clock pulses corresponds to the sampling frequency for the NTSC standard. The digital R, G, B signals are then fed to the video process circuit 13.

In the video process circuit 13, the digital R, G, B signals are transformed to analog video signals and digital video signals. The digital video signals are fed to a computer system 22 via a decoder 25. The digital video signals are subjected to a process in the decoder 25 as described later, and are fed to the computer 22A, in which the process for displaying the object image is performed. Thus, the object image is displayed on the display unit 22B. Note that the display unit 22B corresponds to a computer video standard.

Further, when recording the object image, the digital video signals are fed from the video-processor 10 to the digital recorder 22C, such as a CD-R (Compact Disc-Recordable). recorder, in the computer system 22. The recorder 22 C is provided for recording the object image in a digital image data format.

On the other hand, the analog video signals are fed from the video-processor 10 to the TV monitor 21 so that the object image is displayed on the TV monitor 21. An operator observes the condition of the internal cavity via the displayed image. The timing adjustment circuit 12 has a pulse generator for the video process circuit (not shown). The signal processing in the video process circuit 13 is performed in accordance with clock pulses from the pulse generator.

The system control circuit including a CPU (shown in FIG. 2) controls the electronic endoscope as a whole, and feeds a control signals to the motor drive 17A, the light source 16 and so on. When inputting character information, including patient name, which corresponds to the object image displayed on the TV monitor 21, a keyboard 20 is used. When recording the object image in the digital recorder 22C, panel switches 19 or a push button provided on the video-scope 40 (not shown) are operated. Operation signals, generated by operating the keyboard 20 or the panel switches 19, are input to a peripheral driver 15, and then fed to the system control circuit 14. In an EEPROM 43 provided in the video-scope 40, scope data including a pixel number of the CCD 41 is stored in advance. The scope data is read by the system control circuit 14.

Figure 2:
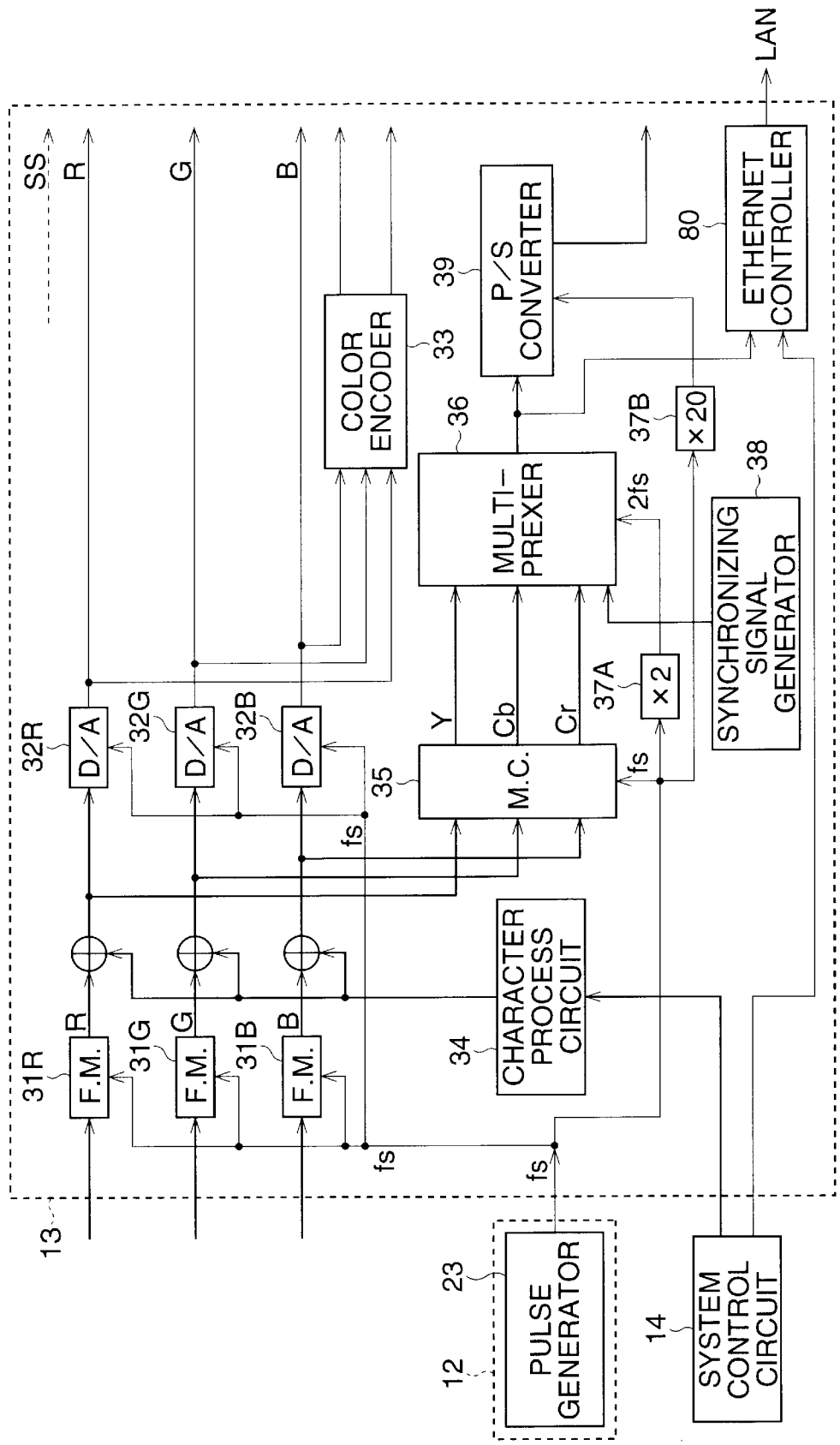
FIG. 2 is a block diagram of a video process circuit.
Figure 3:
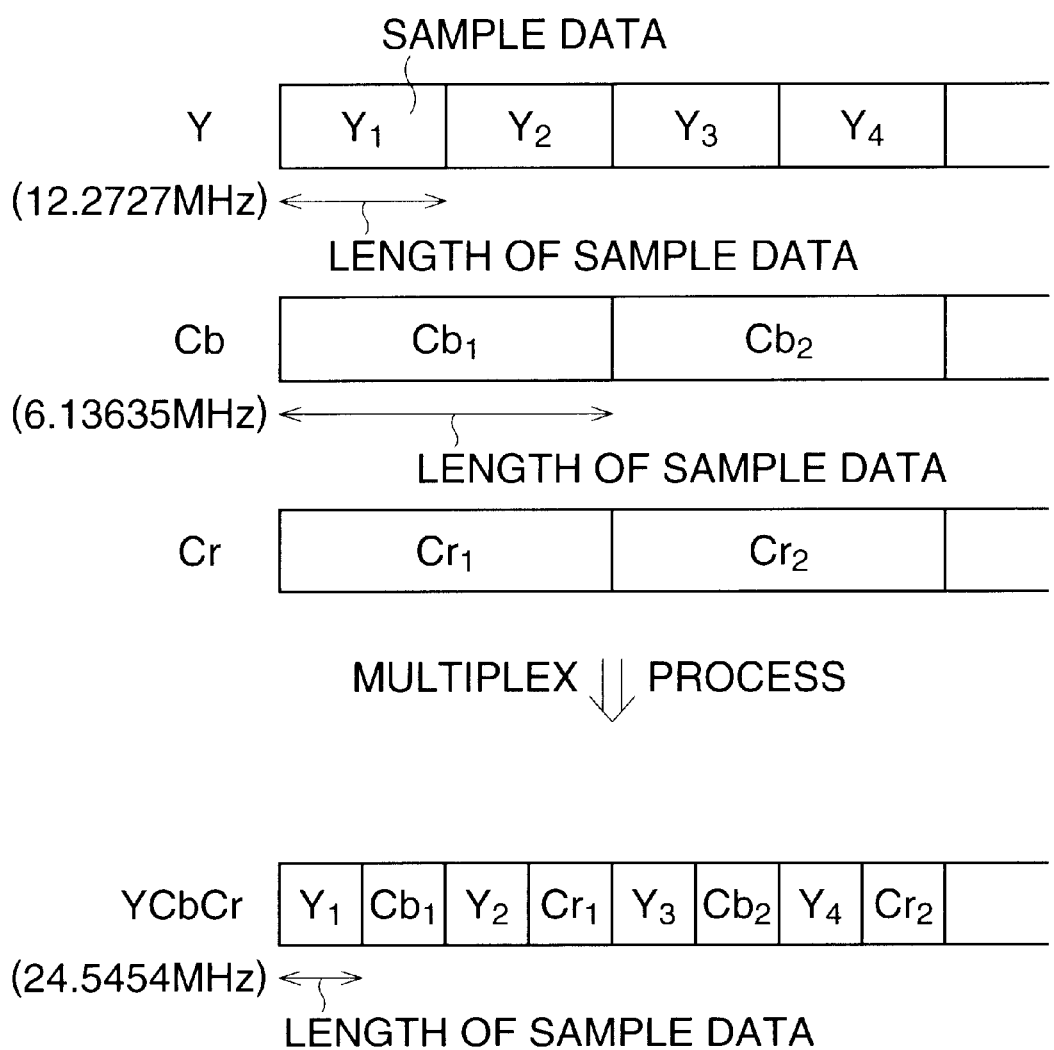
FIG. 3 is a view showing a multiplex process in a multiplexer.
Figure 4:
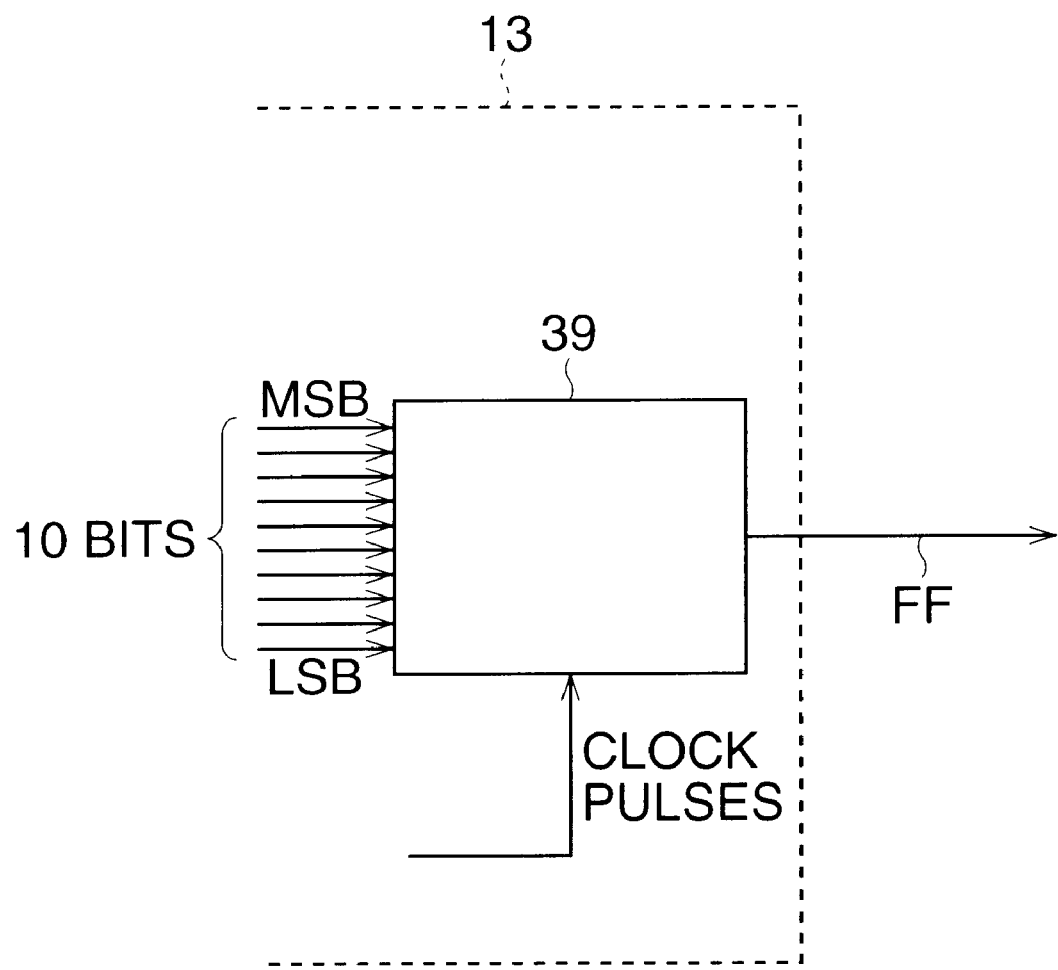
FIG. 4 is a view showing a parallel/serial converter.

FIGS. 2 to 4 refer to the process performed in the video process circuit 13.

FIG. 2 is a block diagram of the video process circuit 13.

The synchronized digital R, G, B signals, input to the video process circuit 13, are temporally stored in a frame memory 31R, a frame memory 31G and a frame memory 31B respectively. The stored digital R, G, B signals are read from the frame memories 31R, 31G, 31B respectively, in accordance with the clock pulses fed from the pulse generator 23 in the timing adjustment circuit 12. The frequency of the clock pulses from the pulse generator 23 is determined by the sampling frequency for digital processing. In this embodiment, the clock frequency corresponds to the sampling frequency for the computer system 22 in place of the sampling frequency for the digital TV standard.

In the case of the digital TV standard, pixels constituting the object image are arranged in a lattice, and the lattice-form, formed by connecting four adjacent pixels each other, is rectangular. Note that, the longitudinal direction of the lattice-form is parallel to the length direction of the screen, on which the image is displayed. On the other hand, in the case of a digital video standard for computers including the computer system 22, pixels constituting the object image are also arranged in a lattice. However, the lattice-form is a square. The pixels with respect to the computer are called "square-pixels". An aspect ratio of the display area with respect to television receivers including the TV monitor 21 and computer apparatus including the display unit 22B is "3:4." Therefore, a pixel number in one line of the computer is fewer than that of the TV. Namely, the sampling frequency for the computer is different from that for the TV. In this embodiment, the sampling frequency for a digital signal processing at the video process circuit 13 corresponds to the computer system 22. Namely, the digital video signals are generated on the basis of the sampling frequency corresponding to the computer video standard. Hereinafter, the sampling frequency corresponding to the computer system 22 is expressed as a "square-pixel frequency".

The square-pixel frequency is obtained by a horizontal scanning frequency of color image signals, called a "line frequency", and the number of pixels in one line. In the NTSC standard, the square-pixel frequency, represented by "$f_s$", is obtained by $$f_s = f_h \times K \quad (1)$$
$$= 15.734 \text{ (kHz)} \times 780$$
$$= 12.2727 \text{ (MHz)}$$

where "$f_h$ (=15.734)" is a horizontal scanning frequency corresponding to the NTSC standard, and "K (=780)" is the number of pixels in one line that correspond to the VGA (Video Graphic Array) standard. Note that, the VGA standard is a representative computer video standard for displaying an image, which has a resolution of "480 (length)× 640 (width)" pixels. In the number of pixels K (=780), the number of effective pixels is "640", and the number of pixels corresponding to a blanking level is "140". Note that, in the case of the digital TV NTSC standard, the number of pixels in one line is "858", including effective pixels of "720", and the sampling frequency is 13.5 MHz.

As described above, the square-pixel frequency $f_s$ is related to the line frequency, which is determined in accordance with the TV standard, and the number of pixels in one line, which is determined in accordance with the computer video standard. Therefore, the square-pixel frequency $f_s$ is determined in accordance with the TV and the computer video standard. In this embodiment, the square-pixel frequency $f_s$ is based on the NTSC method and the VGA standard.

The digital R, G, B signals are read from the frame memory 31R, 31G, 31B respectively, in accordance with the square-pixel frequency $f_s$. Character signals, output from a character process circuit 34, are superimposed into the digital R, G, B signals at a determined timing. The timing of the character signals is controlled by the system control circuit 16. The digital R, G, B signals, including the character signals, are fed to a matrix circuit 35 and D/A converter 32R, 32G and 32B.

In the D/A converters 32R, 32G and 32B, the digital R, G, B signals are transformed to analog R, G, B signals respectively, in accordance with the square-pixel frequency $f_s$. The analog R, G, B signals is output with synchronizing signals (SS) and are fed to a color encoder 33 as analog video signals. In the color encoder 33, the analog R, G, B signals are transformed to composite signals (NTSC composite signals) and component signals (S Video signals). The composite signals and the component signals are output separately. In this embodiment, the composite signals are fed to the TV monitor 21. Note that, the analog video signals are generated in S accordance with the NTSC standard, and synchronizing signals are output from the synchronizing signal generator 38.

On the other hand, in the matrix circuit 35, the digital R, G, B signals are transformed to digital luminance signals Y and digital color difference signals in accordance with the square-pixel frequency $f_s$. The digital color difference signals are composed of signals "Cb (=R−Y)" and signals "Cr (=B−Y)". The ratio of the sampling frequency for the luminance signals Y to the sampling frequency for the color difference signals Cb, Cr is set to "4:2:2". The sampling frequency of the digital luminance signals Y is 12.2727 MHz, equal to the square-pixel frequency $f_s$, and the sampling frequency of the digital color difference signals Cb, Cr is 6.13635 MHz, which is a half of the square-pixel frequency $f_s$. The number of effective pixels in one line with respect to the digital luminance signals Y and the digital color difference signals Cb, Cr is 640, 320, 320, respectively. The number of effective pixels corresponds to the VGA standard. Note that, the ratio of the sampling frequency "4:2:2" is based on a ratio of a sampling frequency with respect to the luminance signals Y and the color difference signals Cb,Cr according to the digital TV standard.

In the multiplexer 36, the digital luminance signals Y and the digital color difference signals Cb, Cr are processed, so that digital multiple signals, or digital video signals, are generated. The clock frequency, identical with the square-pixel frequency $f_s$, is transformed to two times the square-pixel frequency $f_s$ at the operator 37A. Therefore, the multiplex process is performed in accordance with $2f_s$ (=24.5454 MHz) in the multiplexer 36.

In FIG. 3, the luminance signals Y, the color difference signals Cb, Cr and the digital multiple signals are shown.

Sample data of the luminance signals Y, corresponding to the square-pixels, is represented by "Y1, Y2, . . . ". In the same way, each of sample data of the color luminance signals Cb, Cr are "Cb1, Cb2, . . . ", "Cr1, Cr2, . . . " respectively. A length of each sample data corresponds to the magnitude of the sampling frequency. As the sampling frequency is larger, the length of the sample data is smaller. When the multiplex process is performed, the multiple digital video signals are generated such that the sample pixel data is arranged "Y1, Cb1, Y2, Cr1, Y3, Cb2, Y4, Cb2, . . . " as shown in FIG. 3. In addition, timing reference signals (TRS) are added to the digital multiple signals in the multiplexer 36 shown in FIG. 2. Namely, signals corresponding to synchronizing signals are added to blanking intervals between a line of the multiple digital video signal and the next line of the multiple digital video signal. The timing reference signals are output from the synchronizing signal generator 38. The multiple digital video signals are fed to a parallel/serial converter 39 and an Ethernet controller 80.

The Ethernet is a LAN (Local Area Network), which transmits digital parallel signals between networked computer apparatus. The multiple digital video signals output from the multiplexer 36 are digital parallel signals, and the Ethernet controller 80 adjusts the timing of transmission of the digital parallel video signals, thus the digital video signals are able to be transmitted to other networked computer apparatus (not shown). The Ethernet controller 80 is controlled by the system control circuit 16.

On the other hand, in the parallel/serial converter 39, the digital parallel video signals are transformed to digital serial video signals. The frequency of clock pulses for the parallel/serial converter 39 is transformed to 20 times of the square-pixel frequency $f_s$ in the operator 37B, thus the parallel-to-serial conversion is performed in accordance with 20 times the square-pixel frequency $f_s$.

FIG. 4 is a view showing the parallel/serial converter 39. The parallel signals of the digital luminance signals Y and the digital color difference signals Cb, Cr are composed of bit string of 10 bits. Therefore, the digital multiple signals are output from the multiplexer 36 by a bus of 10 bits. In the parallel/serial converter 39, right shift processing from a MSB (Most Significant Bit) to a LSB (Least Significant Bit) and reading of 1 bit data from the LSB are performed alternately. Consequently, the digital serial video signals are generated and then fed to the decoder 25 through a transmitting line FF composed of one bit. Namely, the digital video signals are serial-transmitted. At this time, the serial transmitting bit rate is 245.454 Mbit/s, which corresponds to twelve times of the square-pixel frequency $f_s$.

In this way, the digital video signals are generated in accordance with the square-pixel frequency $f_s$, and then fed to the decoder 25 as serial signals.

Figure 5:
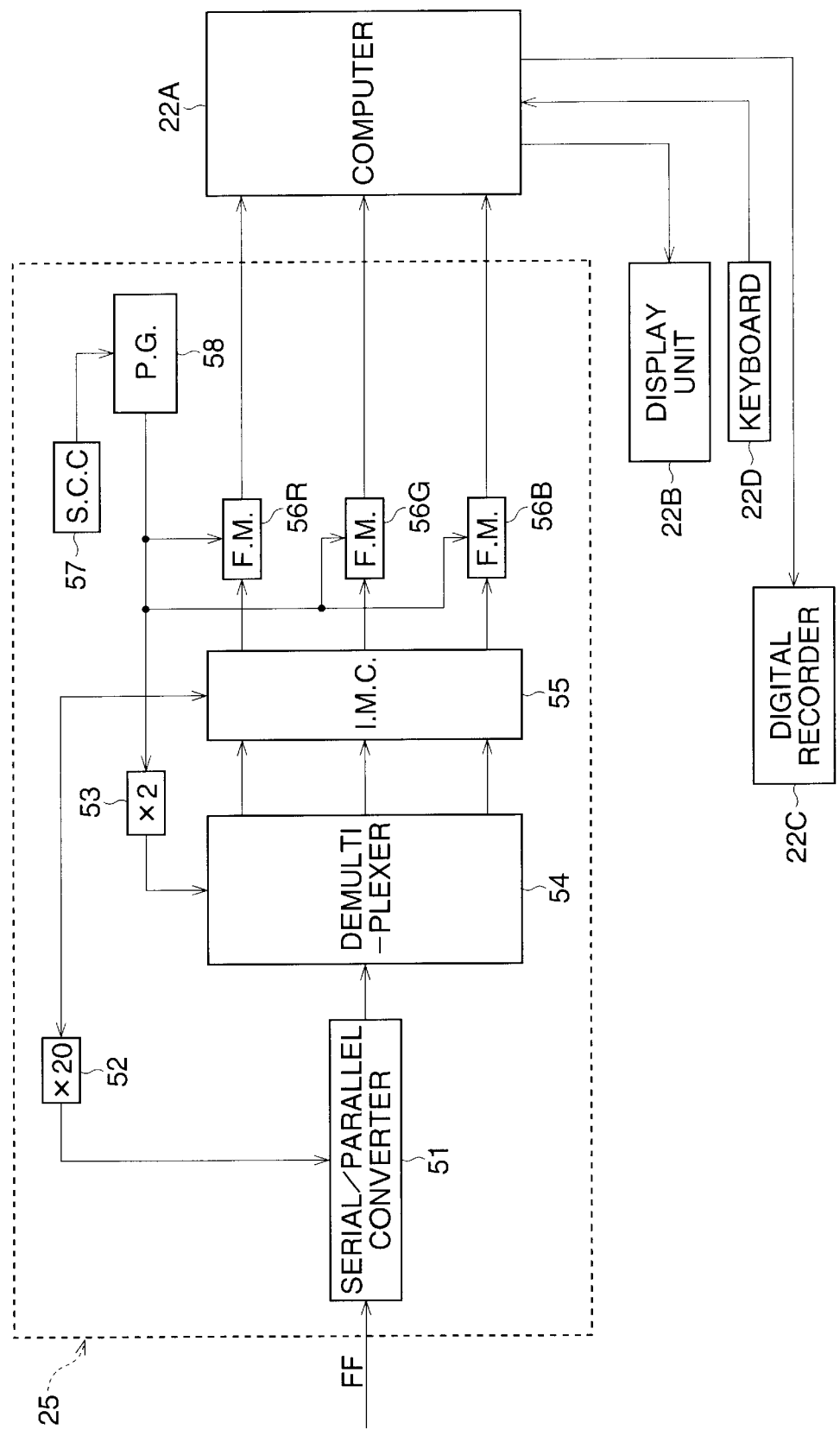
FIG. 5 is a block diagram of a decoder.

FIG. 5 is a view showing a block diagram of the decoder 25. A system control circuit 57 controls the decoder 25.

In a serial/parallel converter 51, the digital serial video signals are transformed to the digital parallel video signals. The digital parallel video signals are then subjected to a demultiplex process at a demultiplexer 54, so that the digital luminance signals Y and the color difference signals Cb,Cr, which are separated respectively, are restored. The digital luminance signals Y and the digital color difference signals Cb, Cr are fed to an inverse matrix circuit 55, in which the digital luminance signals Y and the digital color difference signals Cb, Cr are transformed to the digital R, G, B signals. The digital R, G, B signals are temporally stored in frame memory 56R, 56G, 56B respectively and fed to the computer 22. Note that, the process performed at the serial/parallel converter 51, the demultiplexer 54 and the inverse matrix circuit 55 is an inverse of the process performed at the parallel/serial converter 39, the multiplexer 36 and the matrix circuit 35, which are provided in the video process circuit 13 shown in FIG. 2. The signal process in the decoder 25 is performed in accordance with the square-pixel frequency $f_s$ (=12.2727 MHz), similar to the video process circuit 13 in the video-processor 10. A clock frequency of clock pulses, which corresponds to the square-pixel frequency $f_s$ and is fed from a pulse generator 58, is transformed to 20 times of the square-pixel frequency $f_s$ and transformed to two times the square-pixel frequency $f_s$.

When the digital R, G, B signals are input to the computer 22A, the signals are processed to display the object image on the display unit 22B, which corresponds to the VGA standard. The processed signals are fed to the display unit 22B. Thus, the object image is observed on the display unit 22B. Further, when recording the object image, the digital R, G, B signals are fed to the digital recorder 22C, in which the object image data is recorded in accordance with the square-pixel frequency $f_s$. When many object images are recorded in the recorder 22C, the computer system 22 is used as a filing device. Namely, the object images recorded in the recorder 22C are filed using the keyboard 22D.

The frequency of clock pulses fed from the pulse generator 23 is not restricted to 12.2727 MHz, which is the equal to the square-pixel frequency fs. The clock frequency may be "n" times the square-pixel frequency fs or "1/n" times the square-pixel frequency "fs", where "n" represents integers.

For the color image photographing process, a one chip color method, by which one-chip color filter is provided on the CCD 41 and the rotating filter 17 is deleted, may be applied. Similar to the R, G, B sequential method, the digital R, G, B signals are generated when using the one chip color filter method.

A PAL (Phase Alternation by Line) standard may be applied as the TV standard in place of the NTSC standard. In this case, the square-pixel frequency fs is 14.75 MHz. Therefore, the sampling frequency of the digital luminance signals Y is 14.75 MHz, and the sampling frequency of the digital color difference signals Cb, Cr is 7.375 MHz. Note that, the number of effective pixels in one line with respect to the digital luminance signals Y and the digital color difference signals Cb, Cr are 768, 384, 384 respectively. In the case of the PAL standard, the rotating filter 17 and the CCD 41 are driven in accordance with the PAL standard.

Other video standards for computers, such as SVGA, may be applied in place of the VGA standard. In this case, the square-pixel frequency $f_s$ is determined in accordance with a sampling frequency corresponding to the selected computer video standard.

The multiple digital video signals can be transmitted to the computer system 22 as digital parallel signals in place of the digital serial signals.

The digital serial video signals output from the parallel/serial converter 39 may be directly transmitted to the computer system 22. In this case, the digital serial video signals are fed to the computer 22 bypassing the decoder 25.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 11-265041 (filed on Sep. 20, 1999) which is expressly incorporated herein, by reference, in its entirety.

What is claimed is:

1. A video-processor of an electronic endoscope, to which a video-scope, which includes an image sensor and a computer are connected respectively, an object image being formed on said image sensor, and said video-processor processing image-pixel signals corresponding to the object image that are read from said image sensor, said video-processor comprising:

a video signal processor that generates digital video signals on a basis of the image-pixel signals and output the digital video signals to the computer; and a first pulse generator for said video signal processor that feeds clock pulses to said video signal processor in accordance with a sampling frequency, such that the digital video signals are generated and output in accordance with the sampling frequency;

wherein the sampling frequency corresponds to a square-pixel frequency for the computer.

2. The video-processor of claim 1, wherein the sampling frequency is set to one of "n" times the square-pixel frequency and "1/n" times the square-pixel frequency, where "n" represents integers.

3. The video-processor of claim 1, wherein the image-pixel signals are transformed into digital R, G, B signals, corresponding to red, green and blue colors respectively, by applying a R, G, B sequential method, and said video signal processor includes:

a matrix circuit that transforms the digital R, G, B signals to digital luminance signals and digital color difference signals; and a multiplexer that processes the digital luminance signals and the digital color difference signals so that multiple digital video signals are generated as the digital video signals.

4. The video-processor of claim 3, said multiplexer generates the multiple digital video signals such that a ratio of a sampling frequency of the digital luminance signals and a sampling frequency of the digital color difference signals in the multiplexed digital video signals becomes "4:2:2".

5. The video-processor of claim 4, wherein the clock frequency of clock pulses fed to said matrix circuit is the same as the square-pixel frequency, and the clock frequency of clock pulses fed to said multiplexer is two times the square-pixel frequency.

6. The video-processor of claim 1, wherein a digital recorder for recording the object image as digital image data and a display unit for displaying the object image, which correspond to a computer video standard, are connected to the computer respectively, the digital video signals being fed to said digital recorder and said display unit via the computer.

7. The video-processor of claim 3, wherein said video signal processor further includes a parallel/serial converter that transforms the multiple digital video signals to digital serial video signal to feed digital serial video signals to the computer, said first pulse generator feeding the clock pulses to said parallel/serial converter in accordance with the square-pixel frequency.

8. A decoder in combination with said video-processor in claim 7, said decoder provided between said video-processor and the computer for feeding the digital R, G, B signals to the computer, said decoder comprising:

a serial/parallel converter that transforms the digital serial video signals to the multiple digital video signals;

a demultiplexer that processes the multiple digital video signals so as to restore the digital luminance signals and the digital color difference signals;

an inverse matrix circuit that transforms the digital luminance signals and the digital color difference signals to the digital R, G, B signals; and a second pulse generator for said decoder that feeds clock pulses to said serial/parallel converter, said demultiplexer and said inverse matrix circuit in accordance with the square-pixel frequency.

9. A video-processor of an electronic endoscope connected to an image sensor and a processor, said video-processor comprising:

a video signal processor that generates digital video signals on a basis of image-pixel signals and outputs digital video signals to the processor; and a first pulse generator that feeds clock pulses to said video signal processor in accordance with a sampling frequency, such that the digital video signals are generated and output in accordance with the sampling frequency;

wherein the sampling frequency corresponds to a square-pixel frequency of the processor.

10. The video-processor of claim 9, wherein the sampling frequency is set to one of "n" times the square-pixel frequency and "1/n" times the square-pixel frequency, where "n" is an integer.

11. The video-processor of claim 9, wherein the image-pixel signals are transformed into digital R, G, B signals, corresponding to red, green and blue colors respectively, by applying a R, G, B sequential method, and said video signal processor comprising:

a matrix circuit that transforms the digital R, G, B signals to digital luminance signals and digital color difference signals; and a multiplexer that processes the digital luminance signals and the digital color difference signals so that multiple digital video signals are generated as the digital video signals.

12. The video-processor of claim 9, wherein a digital recorder for recording an object image as digital image data and a display unit for displaying the object image, which correspond to a computer video standard, are connected to the processor, the digital video signals being fed to said digital recorder and said display unit via the processor.

13. A method of using a video-processor of an electronic endoscope connected to an image sensor and a processor, the method comprising:

generating digital video signals on a basis of image-pixel signals and outputting digital video signals to the processor; and feeding clock pulses to a video signal processor in accordance with a sampling frequency, such that the digital video signals are generated and output in accordance with the sampling frequency;

wherein the sampling frequency corresponds to a square-pixel frequency of the processor.

14. The method of claim 13, wherein the sampling frequency is set to one of "n" times the square-pixel frequency and "1/n" times the square-pixel frequency, where "n" is an integer.

15. The method of claim 13, wherein the image-pixel signals are transformed into digital R, G, B signals, corresponding to red, green and blue colors respectively, by applying a R, G, B sequential method, and the method further includes:

transforming the digital R, G, B signals to digital luminance signals and digital color difference signals; and processing the digital luminance signals and the digital color difference signals so that multiple digital video signals are generated as the digital video signals.

* * * * *